(12) United States Patent
Watanabe et al.

(10) Patent No.: US 8,518,423 B2
(45) Date of Patent: Aug. 27, 2013

(54) METHOD FOR ENHANCING CHROMA OF HAIR

(75) Inventors: Shunsuke Watanabe, Tokyo (JP);
Satoshi Shibuichi, Tokyo (JP);
Toshihiko Matsui, Tokyo (JP)

(73) Assignee: KAO Corporation, Tokyo (JP)

( * ) Notice: Subject to any disclaimer, the term of this patent is extended or adjusted under 35 U.S.C. 154(b) by 1197 days.

(21) Appl. No.: 11/316,746

(22) Filed: Dec. 27, 2005

(65) Prior Publication Data
US 2006/0140900 A1 Jun. 29, 2006

(30) Foreign Application Priority Data
Dec. 28, 2004 (JP) .................................. 2004-381328

(51) Int. Cl.
*A61K 8/02* (2006.01)
(52) U.S. Cl.
USPC .... 424/401; 424/70.1; 424/70.11; 424/70.12; 424/70.28; 514/880; 514/881
(58) Field of Classification Search
None
See application file for complete search history.

(56) References Cited

U.S. PATENT DOCUMENTS

| | | | | |
|---|---|---|---|---|
| 4,472,297 A * | 9/1984 | Bolich et al. | .................. | 510/121 |
| 5,077,040 A | 12/1991 | Bergmann et al. | | |
| 6,143,286 A | 11/2000 | Bhambhani et al. | | |
| 6,602,494 B1 | 8/2003 | Jahedshoar et al. | | |
| 7,147,843 B2 * | 12/2006 | Yoshida et al. | .............. | 424/70.9 |
| 2002/0006389 A1 | 1/2002 | Restle et al. | | |
| 2003/0003073 A1 | 1/2003 | Muller | | |

FOREIGN PATENT DOCUMENTS

| | | |
|---|---|---|
| EP | 1 258 236 A1 | 11/2002 |
| EP | 1 468 665 A2 | 10/2004 |
| JP | 63-51315 | 3/1988 |
| JP | 5-345707 | 12/1993 |
| JP | 2000-72631 | 3/2000 |
| JP | 2001-220321 | 8/2001 |
| JP | 2001-220322 | 8/2001 |
| JP | 2003-119116 | 4/2003 |
| JP | 2004-35434 | 2/2004 |
| WO | WO 03/066007 A1 | 8/2003 |
| WO | WO 03/105792 A1 | 12/2003 |
| WO | WO 2004/014334 A1 | 2/2004 |

OTHER PUBLICATIONS

Safety data for dimethicone, [online], Retrieved [Jul. 22, 2009], Retrieved from URL:<http://msds.chem.ox.ac.uk/DI/dimethicone.html>.*
Brett Moss, et al., "Silicones as a Color-Lock Aid in Rinse-Off Hair Care Products", URL:http://www.dowcorning.com/content/publishedlit/27-1152-01.pdf>, XP-002375057, pp. 1-5.
Notice of Opposition issued Sep. 23, 2010, in Europe Patent Application No. 05028577.4 (with English-language Translation).
Marianne D. Berthiaume, et al., "Effects of silicone pretreatment on oxidative hair damage", J. Soc. Cosmet. Chem., vol. 46, Sep./Oct. 1995, pp. 231-245 (with an additional page).
Gerhard Meir, et al., "Beautiful Hair", Midena Verlag Munich, 2000, 7 pages (with English-language Translation).
"The Book of the 250 Top Hairstyles", Journal Ullstein for Women, Ullstein Buchverlage, 1997, 18 pages (with English-language Translation).
Wilfried Umbach, "Cosmetics: Development, production and use of cosmetic compositions", Georg Thieme Verlag Stuttgart, 1988, 21 pages (with English-language Translation).
Karlheinz Schrader, "Fundamentals and formulations of cosmetics", Hüthig Verlag, 2nd edition, 1989, 13 pages (with English-language Translation).

* cited by examiner

*Primary Examiner* — Lezah Roberts
*Assistant Examiner* — Nannette Holloman
(74) *Attorney, Agent, or Firm* — Oblon, Spivak, McClelland, Maier & Neustadt, L.L.P.

(57) ABSTRACT

There is provided a method for enhancing a chroma of hair which comprises the steps of shampooing the hair with a water-based shampoo containing (A) 5 to 20% by weight of an anionic surfactant, (B) 0.1 to 5% by weight of a water-insoluble modified silicone containing at least one of an amino group and a quaternary ammonium group in a molecule thereof, and (C) a water-soluble salt in an amount capable of allowing the component (B) to be present in a solubilized state; applying a water-based conditioner containing a higher alcohol having 12 to 28 carbon atoms and a cationic surfactant at a molar ratio of 1:1 to 10:1 to the shampooed hair; and rinsing the hair. The method is capable of allowing an inherent color of hair, a dull color of damaged hair or a color of hair dyed by coloring to look clearer or more vivid, or maintaining a clearness of the color of hair.

18 Claims, No Drawings

METHOD FOR ENHANCING CHROMA OF HAIR

FIELD OF THE INVENTION

The present invention relates to a method for enhancing the chroma of hair by shampooing the hair with a water-based shampoo and then treating the hair with a water-based conditioner.

BACKGROUND OF THE INVENTION

One of methods for making hair look beautiful is to enhance luster of the hair. In order to realize enhanced luster of hair, there have been used various methods such as a method of enhancing smoothness on a surface of hair to suppress light scattering thereon, and a method of improving the manageability of a hair bundle to form a large reflection surface thereon and generate a sharp reflected light therefrom.

Other effective methods for making hair look beautiful include the method of rendering a color of hair clear or vivid, for example, by applying a hair color, etc., to the hair to add a fresh bright color thereto (coloring, etc.). As a result of the coloring, etc., a youthful look or vivid look is imparted to persons, leading to a personal image-change. In the coloring method, etc., although the color of hair may be changed quite differently, an inherent natural color of the hair itself is not caused to look clear or vivid. Further, the hair dyed by the coloring method tends to be undesirably discolored by degradation and deterioration of dyes owing to UV radiation and oxidation, or by elution of the dyes owing to repeated treatments with shampoo or conditioner.

To solve the problems, there is a generally known method of blending an ultraviolet absorber, an antioxidant or a silicone compound in the shampoo or conditioner to inhibit the discoloration of hair. For example, it has been reported that hair dyed by coloring is treated with a conditioner blended with an amino-modified silicone to prevent discoloration of the hair due to shampooing (refer to "JOURNAL OF COSMETIC SCIENCE, 2003 ANNUAL SCIENTIFIC MEETING", p. 130). Also, it has been reported that silicones are blended in a shampoo to inhibit discoloration of colored hair due to shampooing (refer to U.S. Pat. No. 5,609,861 and US 2003/0198615A). These methods are effective to reduce the speed of discoloration of colored hair, but do not serve for allowing the color of the hair to positively look clear or vivid.

Also, there are known shampoos or conditioners directly blended with dyes or pigments (refer to PCT pamphlets Nos. WO 03/055457, WO 01/78670 and WO 01/78671). These shampoos or conditioners are effective to render the color of hair vaguely clear or vivid and compensate for the discoloration of colored hair, but do not serve for allowing natural color of the hair or a color of the hair dyed to look natural and clear or vivid.

SUMMARY OF THE INVENTION

The present invention provides a method for enhancing the chroma of hair, including the steps of:

shampooing the hair with a water-based shampoo containing (A) 5 to 20% by weight of an anionic surfactant, (B) 0.1 to 5% by weight of a water-insoluble modified silicone containing at least one of an amino group and a quaternary ammonium group in a molecule thereof, and (C) a water-soluble salt in an amount capable of allowing the component (B) to be present in a solubilized state;

applying a water-based conditioner containing a higher alcohol having 12 to 28 carbon atoms and a cationic surfactant at a molar ratio of 1:1 to 10:1 to the shampooed hair; and rinsing the hair.

DETAILED DESCRIPTION OF THE INVENTION

In accordance with the present invention, there is provided a method for allowing an inherent color of hair, a dull color of damaged hair, or a color of hair dyed look clearer or more vivid by using a water-based shampoo containing a water-insoluble modified silicone and a water-soluble salt in combination with a water-based conditioner containing a higher alcohol and a cationic surfactant.

The present inventors have found that a color of hair is rendered clear or vivid by shampooing the hair with a water-based shampoo containing a specific modified silicone in a solubilized state, and then treating the hair with a water-based conditioner containing a higher alcohol and a cationic surfactant at a specific mixing ratio. The present invention has been accomplished on the basis of this finding.

The preferred embodiments of the present invention are described below.

[Water-based Shampoo]

The water-based shampoo of the present invention contains an aqueous medium, and an anionic surfactant and a specific water-insoluble modified silicone which are included in the aqueous medium, and further contains a water-soluble salt in an amount capable of allowing the water-insoluble modified silicone to be present in a solubilized state. Here, the "solubilized state" of the modified silicone means such a condition in which the water-insoluble modified silicone is non-isolated in the water-based shampoo, and any particles of the modified silicone are unobserved by the naked eyes or an optical microscope. More specifically, in the solubilized state, the water-based shampoo exhibits a transparent appearance when observed by the naked eyes, or no particles are recognized therein even when observed by an optical microscope at a magnification of 1000 times.

Examples of the anionic surfactant include sulfonate-type surfactants, carboxylate-type surfactants and sulfuric acid-based anionic surfactants. Specific examples of the sulfonate-type surfactants and carboxylate-type surfactants include salts of sulfosuccinic acid alkyl esters, salts of polyoxyalkylene sulfosuccinic acid alkyl esters, higher fatty acid salts, alkanesulfonic acid salts, and alkylethercarboxylic acids or salts thereof. Specific examples of the sulfuric acid-based anionic surfactants include sulfates of polyoxyethylene alkyl ether, sulfates of polyoxyethylene alkenyl ethers, alkyl sulfates and sulfates of polyoxyalkylene alkyl phenyl ethers.

Among these anionic surfactants, preferred are sulfuric acid-based anionic surfactants, and more preferred are those sulfuric acid-based anionic surfactants represented by the following general formula (1) or (2):

$$R^1O(CH_2CH_2O)_mSO_3M \qquad (1), or$$

$$R^2OSO_3M \qquad (2)$$

wherein $R^1$ is an alkyl group or an alkenyl group having 10 to 18 carbon atoms; $R^2$ is an alkyl group having 10 to 18 carbon atoms; M is an alkali metal, an alkali earth metal, ammonium, alkanol amine or a basic amino acid; m is a number of 1 to 5 in weight-average.

These anionic surfactants may be used alone or in combination of any two or more thereof. The content of the anionic surfactant in the water-based shampoo of the present invention is preferably from 5 to 20% by weight and more preferably from 10 to 17% by weight in view of a good stability of the water-based shampoo, liquid properties thereof upon use, easiness of foaming or lathering, and easiness of shampooing.

The water-insoluble modified silicone as the component (B) of the present invention contains at least one of an amino group and a quaternary ammonium group in a molecule thereof. Examples of the water-insoluble modified silicone include the following amino-modified silicones and quaternary compounds obtained by replacing amino groups of the amino-modified silicones with a lower alkyl group, etc. (hereinafter referred to as (B-1), (B-2) and (B-3)). These water-insoluble modified silicones may be used together with a surfactant in the form of a water-based emulsion.

(B-1): Compounds having an average molecular weight of about 3000 to 100000 which are described under the name of "Amodimethicone" in INCI Dictionary (US, International Cosmetic Ingredient Dictionary and Handbook), 10th Edition.

(B-2) Water-insoluble amino-modified silicones represented by the general formula (3):

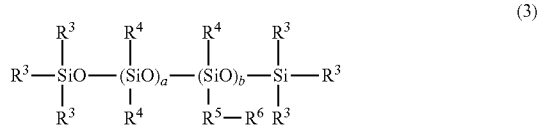

wherein $R^3$ groups are each independently a monovalent hydrocarbon group, a hydroxyl group or an alkoxy group; $R^4$ groups are each independently a monovalent hydrocarbon group; $R^5$ groups are each independently a divalent hydrocarbon group having 1 to 10 carbon atoms; $R^6$ groups are each independently a group represented by the following general formula (4):

wherein Y groups are each independently a hydrogen atom or a group represented by the general formula: —$CH_2$—$CH(OH)$—$R^5$—OH wherein $R^5$ has the same meaning as defined above; and $R^7$ groups are each independently a hydrogen atom or a group represented by the general formula: —$R^5NY_2$ wherein Y and $R^5$ have the same meanings as defined above with the proviso that all of the Y groups are not a hydrogen atom at the same time; a is a number of 25 to 1000; and b is a number of 1 to 200.

Examples of the monovalent hydrocarbon group as $R^3$ include an alkyl group and an aryl group. Among these groups as $R^3$, preferred are alkyl groups having 1 to 3 carbon atoms, especially methyl, as well as alkoxy groups having 1 to 15 carbon atoms and preferably 10 to 15 carbon atoms.

Examples of the monovalent hydrocarbon group as $R^4$ include an alkyl group having 1 to 6 carbon atoms such as methyl, ethyl, propyl, butyl, pentyl and hexyl; an aryl group having 6 to 10 carbon atoms such as phenyl, tolyl and xylyl; and an aralkyl group having 6 to 10 carbon atoms such as benzyl and phenethyl. Among these groups, preferred are alkyl groups having 1 to 3 carbon atoms, and more preferred is methyl.

Examples of the divalent hydrocarbon group having 1 to 10 carbon atoms as $R^5$ include an alkylene group such as methylene, ethylene, trimethylene, propylene, tetramethylene, methyltrimethylene, ethylethylene and dimethylethylene; and an alkylene arylene group such as the group represented by the formula: —$(CH_2)_2$—$C_6H_4$—. Among these groups, preferred are alkylene groups having 2 to 4 carbon atoms.

The preferred group as $R^6$ includes those groups represented by the general formula (4). The preferred group as $R^7$ in the general formula (4) includes N-(2,3-dihydroxypropyl)aminoethyl and N,N,-bis(2,3-dihydroxypropyl)aminoethyl. Among the groups represented by the general formula: —$CH_2$—$CH(OH)$—$R^5$—OH as Y, preferred is 2,3-dihydroxypropyl.

As the amino-modified silicone represented by the general formula (3), there may be used, for example, "DC 8500" commercially available from Toray-Dow Corning Co., Ltd.

(B-3) Block polymers containing a polymer unit composed of a polyalkylene chain and an amino-modified organosiloxane chain represented by the general formula (5):

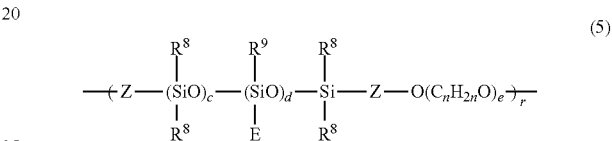

wherein $R^8$ is a hydrogen atom or a monovalent hydrocarbon group having 1 to 6 carbon atoms; $R^9$ is either $R^8$ or E; E is a reactive functional group represented by the general formula: —$R^{10}$—W wherein $R^{10}$ is a direct bond or a divalent hydrocarbon group having 1 to 20 carbon atoms and W is a primary to tertiary amino-containing group or an ammonium-containing group; a plurality of $R^8$ groups, a plurality of $R^9$ groups, a plurality of $R^{10}$ groups and a plurality of E groups may be respectively the same or different; Z is a divalent organic group which is bonded to an adjacent silicon atom through a carbon-silicon bond and to a polyoxyalkylene block chain through an oxygen atom; n is a number of 2 to 10, and n's in number of e may be the same or different; c is a number of 2 or more; d is a number of 1 or more; e is a number of 4 or more; and f is a number of 2 or more.

Examples of the preferred divalent organic group represented by Z in the general formula (5) include an alkylene group and an arylene group. Among these groups, more preferred are alkylene groups having 1 to 12 carbon atoms and arylene groups having 6 to 12 carbon atoms, even more preferred are ethylene, propylene, trimethylene, n-butylene and i-butylene, and even more preferred are n-butylene and i-butylene. The suffix c is preferably a number of 2 to 1000, d is preferably a number of 1 to 50, e is preferably a number of 4 to 200, and f is preferably a number of 2 to 100.

Examples of the water-insoluble amino-modified silicone represented by the general formula (5) include "FZ-3789" commercially available from Nippon Unicar Co., Ltd.

Examples of the water-soluble salt used as the component (C) in the present invention include inorganic acid salts such as hydrochlorides, sulfates, nitrates, phosphates and chlorates; and organic acid salts such as acetates, citrates, malates, lactates and oxalates. Examples of the cations contained in the water-soluble salts include monovalent ions such as lithium ion, potassium ion, sodium ion and ammonium ion; and polyvalent ions such as calcium ion, magnesium ion and aluminum ion. These water-soluble salts exhibit a property of increasing a solubilizing power of the anionic surfactant, and allow the component (B) to be solubilized under the coexistence of the component (A). In view of good stability, liquid properties, feel to the touch and flexibility of the composition in addition to the above solubilizing performance, among these water-soluble salts, preferred are hydrochlorides, sulfates, citrates, malates and lactates. Among the cations contained in these water-soluble salts, preferred are sodium ion and ammonium ion. The more preferred water-soluble salt is sodium sulfate.

The content of the component (C) in the water-based shampoo is controlled to such an amount in which the component (B) is allowed to be present in a solubilized state in the composition containing whole surfactants including, in addition to the component (A), amphoteric surfactant and nonionic surfactant, if added, the component (B), the component (C) and water. The upper limit of the content of the component (C) is the amount in which the surfactant(s) suffers from no phase separation, whereas the lower limit of the content of the component (C) is the amount in which the solubilized state of the component (B) is recognized when observed by an optical microscope. In particular, the content of the component (C) is preferably controlled to such an amount in which a solution containing whole surfactants, the component (B), the component (C) and water exhibits an optical flow birefringence.

In general, it is considered that when the amount of the water-soluble salt added to an aqueous ionic surfactant solution having an optical isotropy is increased, the solution is transformed into a liquid crystal state and exhibits an optical anisotropy when the amount of the water-soluble salt added reaches a certain value. The amount of the water-soluble salt added to the aqueous ionic surfactant solution in which the solution undergoes the transformation into a liquid crystal state tends to depend upon the kind and concentration of the ionic surfactant used as well as kind of the water-soluble salt added. It is also considered that, between the region of concentration of the water-soluble salt in which the solution shows an optical isotropy and the region in which the solution shows an optical anisotropy, there generally exists a flow birefringence region as an intermediate region in which the solution exhibits an isotropic phase when kept in a static state but the solution exhibits an anisotropic phase when tilted or shaken.

The content of the component (C) in the water-based shampoo strongly depends upon amounts and kinds of the components (A) and (B) used and, therefore, may be appropriately adjusted within the range of from 0.001 to 20% by weight so as to satisfy the above conditions for the components (A) and (B). In particular, the content of the component (C) is preferably controlled to such a range in which the water-based shampoo shows the above flow birefringence, and more preferably in the range of from 0.1 to 10% by weight in which the water-based shampoo shows the flow birefringence under the coexistence of the components (A) and (B).

The water-based shampoo of the present invention may further contain a nonionic surfactant, an amphoteric surfactant or a mixture thereof to improve liquid properties, stability, washing performance, easiness of foaming or lathering, quality of foam, etc.

Examples of the nonionic surfactant include polyoxyalkylene sorbitan fatty esters, polyoxyalkylene sorbitol fatty esters, polyoxyalkylene glycerol fatty esters, polyoxyalkylene fatty esters, polyoxyalkylene alkyl ethers, polyoxyalkylene alkyl phenyl ethers, polyoxyalkylene (hardened) castor oils, sucrose fatty esters, polyglycerol alkyl ethers, polyglycerol fatty esters, fatty acid alkanol amides, alkyl glyceryl ethers and alkyl glycosides. Among these nonionic surfactants, preferred are alkyl glycosides, polyoxyalkylene fatty ($C_8$ to $C_{20}$) esters, polyoxyethylene sorbitan fatty esters, polyoxyethylene hardened castor oils, fatty acid alkanol amides and alkyl glyceryl ethers. The fatty acid alkanol amides are preferably those containing an acyl group having 8 to 18 carbon atoms and preferably 10 to 16 carbon atoms, and may be in the form of either a monoalkanol amide or a dialkanol amide. Further, the fatty acid alkanol amides are more preferably those containing a hydroxyalkyl group having 2 to 3 carbon atoms. Specific examples of the fatty acid alkanol amides include oleic acid diethanol amide, palm kernel oil fatty acid diethanol amide, coconut oil fatty acid diethanol amide, lauric acid diethanol amide, polyoxyethylene coconut oil fatty acid monoethanol amide, coconut oil fatty acid monoethanol amide, lauric acid isopropanol amide and lauric acid monoethanol amide.

These nonionic surfactants may be used in combination of any two or more thereof. The content of the nonionic surfactant in the water-based shampoo of the present invention is preferably from 0.1 to 10% by weight, more preferably from 0.2 to 7% by weight and still more preferably from 0.5 to 5% by weight in view of good stability of the shampoo, good liquid properties upon use, easiness of foaming or lathering, easiness of shampooing and fine soft foam quality.

Examples of the preferred amphoteric surfactant include betaine-based surfactants such as alkyldimethylaminoacetic acid betaines, alkylcarboxymethylhydroxyethyl imidazolium betaines and fatty amide propyl betaines. Among these betaine-based surfactants, more preferred are fatty amide propyl betaines. The fatty amide propyl betaines are preferably those containing an acyl group having 8 to 18 carbon atoms and more preferably 10 to 16 carbon atoms. Specific examples of the fatty amide propyl betaines include lauramide propyl betaine, palm kernel oil fatty amide propyl betaine and coconut oil fatty amide propyl betaine.

These amphoteric surfactants may be used in combination of any two or more thereof The content of the amphoteric surfactant in the water-based shampoo of the present invention is preferably from 0.1 to 10% by weight, more preferably from 0.2 to 7% by weight and still more preferably from 0.5 to 5% by weight in view of good stability of the shampoo, good liquid properties upon use, easiness of foaming or lathering, easiness of shampooing and fine soft foam quality.

The water-based shampoo of the present invention may further contain, in addition to the above components, other components or various additives according to requirements. Examples of the other components and additives include thickening agents such as hydroxyethyl cellulose, polyvinyl alcohol and carboxyvinyl polymers; oils such as hydrocarbon oils, waxes, ester oils, dimethyl polysiloxane and polyether-modified silicones; conditioning agents such as cationated cellulose and cationated guar gum; polyhydric alcohols such as glycerol and propylene glycol; organic solvents such as benzyl alcohol and ethanol; pearling agents such as fatty acid glycol esters; ultraviolet absorbers such as benzoic acid-based absorbers, acetolanilic acid-based absorbers, salicylic acid-based absorbers, cinnamic acid-based absorbers and benzophenone-based absorbers; antioxidants such as vitamin E and derivatives of vitamin E; preservatives such as parabene; germicides or anti-dandruff agents such as salicylic acid, trichlosan, piroctone-olamine and zinc pyrithione; pH controllers such as sodium hydroxide, potassium hydroxide, citric acid and malic acid; sequestering agents such as edetic acid salts and hydroxyethane diphosphonic acid; and other extracts and dyes derived from animals and plants.

[Water-based Conditioner]

The water-based conditioner of the present invention contains an aqueous medium, and a higher alcohol and a cationic surfactant which are contained in the aqueous medium at a molar ratio of from 1:1 to 10:1. In particular, in view of good emulsion stability and good smoothness upon application and rinsing, the molar ratio of the higher alcohol to the cationic surfactant is preferably from 1.5:1 to 7:1, more preferably from 2:1 to 5:1 and even more preferably from 2:1 to 4:1.

Examples of the higher alcohol include cetyl alcohol, stearyl alcohol, arachyl alcohol, behenyl alcohol, 2-octyldodecanol, 2-hexyldecyl alcohol, isostearyl alcohol and carnaubyl alcohol (tetracosanol). Among these higher alcohols, preferred are stearyl alcohol, behenyl alcohol and a mixture thereof These higher alcohols may be used alone or in combination of any two or more thereof The content of the higher alcohol in the water-based conditioner of the present invention is preferably from 1 to 10% by weight, more preferably from 1.5 to 8% by weight and even more preferably from 2 to 5% by weight in view of imparting the wet hair with a good finger passing property and good smoothness and the dried hair with softness, as well as in view of good emulsion stability of the water-based conditioner.

Examples of the cationic surfactant include quaternary ammonium salts, tertiary amine compounds and acid-added salts thereof which have one or two hydrophobic chains therein.

The quaternary ammonium salt-type cationic surfactant and the tertiary amine-type cationic surfactant are preferably compounds represented by the following general formulae (6) and (7), respectively:

(6)

wherein A is a hydrogen atom or a linear or branched saturated or unsaturated amido, N-hydrocarbon carbamoyl, acyloxy or hydrocarbon oxy group having 12 to 28 carbon atoms in total; B is a divalent linear or branched saturated or unsaturated hydrocarbon group having 1 to 28 carbon atoms; at least one of $R^{11}$, $R^{12}$ and $R^{13}$ is a linear or branched alkyl or alkenyl group having 1 to 24 carbon atoms in total, and the remainder of $R^{11}$, $R^{12}$ and $R^{13}$, if any, is an alkyl group having 1 to 3 carbon atoms; and $X^-$ is a halide ion or an organic anion, and

(7)

wherein A and B have the same meanings as defined above; and $R^{14}$ and $R^{15}$ are each independently an alkyl group having 1 to 4 carbon atoms.

Examples of the quaternary ammonium salt-type cationic surfactant represented by the general formula (6) include mono-long chain alkyl (carbon number: 12 to 28) quaternary ammonium salts, di-long chain alkyl (carbon number: 12 to 28) quaternary ammonium salts, branched alkyl (carbon number: 12 to 28) quaternary ammonium salts, alkylamido (carbon number: 12 to 28) alkyl (carbon number: 1 to 5) quaternary ammonium salts, N-hydrocarbon (carbon number: 12 to 28) carbamoyl alkyl (carbon number: 1 to 5) quaternary ammonium salts, acyl (carbon number: 12 to 28) oxy alkyl (carbon number: 1 to 5) quaternary ammonium salts, and alkyl or alkenyl (carbon number: 12 to 28) oxy alkyl (carbon number: 1 to 5) quaternary ammonium salts.

Specific examples of the mono-long chain alkyl (carbon number: 12 to 28) quaternary ammonium salts include stearyl trimethyl ammonium chloride, myristyl trimethyl ammonium chloride, cetyl trimethyl ammonium chloride, arachyl trimethyl ammonium chloride, behenyl trimethyl ammonium chloride, lauryl trimethyl ammonium chloride, N-stearyl-N,N,N-tri(polyoxyethylene) ammonium chloride (total molar number of addition: 3 mol).

Specific examples of the di-long chain alkyl or alkenyl (carbon number: 12 to 28) quaternary ammonium salts include distearyl dimethyl ammonium chloride, dioleyl dimethyl ammonium chloride, dipalmityl methylhydroxyethyl ammonium methosulfate, diisostearyl dimethyl ammonium methosulfate, di[(2-dodecanoylamino)ethyl]dimethyl ammonium chloride, and di[(2-stearoylamino)propyl]dimethyl ammonium ethosulfate.

Specific examples of the branched alkyl (carbon number: 12 to 28) quaternary ammonium salts include 2-decyltetradecyl trimethyl ammonium chloride, 2-dodecylhexadecyl trimethyl ammonium chloride, di-2-hexyldecyl dimethyl ammonium chloride and di-2-octyldodecyl dimethyl ammonium chloride.

Specific examples of the alkylamido (carbon number: 12 to 28) alkyl (carbon number: 1 to 5) quaternary ammonium salts include stearamidopropyl quaternary ammonium salts. Specific examples of the N-hydrocarbon (carbon number: 12 to 28) carbamoyl alkyl (carbon number: 1 to 5) quaternary ammonium salts include N-stearylcarbamoyl propyl quaternary ammonium salts. Specific examples of the acyl (carbon number: 12 to 28) oxy alkyl (carbon number: 1 to 5) quaternary ammonium salts include stearyloxypropyl quaternary ammonium salts. Specific examples of the hydrocarbon (carbon number: 12 to 28) oxy alkyl (carbon number: 1 to 5) quaternary ammonium salts include octadecyloxypropyl trimethyl ammonium chloride.

In the tertiary amine-type compound represented by the general formula (7), A other than a hydrogen atom is preferably an amido group or a hydrocarbon-oxy group having 14 to 22 carbon atoms in total and preferably 18 to 22 carbon atoms in total, and more preferred are those groups containing a saturated hydrocarbon moiety and preferably a saturated linear hydrocarbon moiety. In such a case, B is preferably a trimethylene group. When A is a hydrogen atom, B is preferably a group having 18 to 22 carbon atoms, more preferably a saturated group having 18 to 22 carbon atoms and still more preferably a saturated linear group having 18 to 22 carbon atoms. Examples of the group as $R^{14}$ and $R^{15}$ include methyl, ethyl, propyl, isopropyl, butyl and t-butyl. Among these group, preferred are methyl and ethyl, and more preferred is methyl. Specific examples of the preferred tertiary amine-type compound include N,N-dimethyloctadecyloxypropyl amine and stearamidopropyldimethyl amine.

The tertiary amine-type compound represented by the general formula (7) may be directly used as the tertiary amine-type cationic surfactant, or may also be used in the form of an acid-added salt thereof. In any cases, it is required to dissociate the amine by acidifying the water-based conditioner. As the acid for forming the acid-added salt or acidifying the water-based conditioner, there may be used acidic amino acids, organic acids and inorganic acids.

Examples of the acidic amino acids include glutamic acid and aspartic acid. Examples of the organic acids include carboxylic acids such as monocarboxylic acids, dicarboxylic acids, hydroxycarboxylic acids and polycarboxylic acids; alkylsulfuric acids; and alkylphosphoric acids. Among these organic acids, preferred are carboxylic acids, and more preferred are dicarboxylic acids and hydroxycarboxylic acids. Specific examples of the dicarboxylic acids include malonic acid, succinic acid, glutaric acid, adipic acid, maleic acid, fumaric acid and phthalic acid. Specific examples of the hydroxycarboxylic acids include glycolic acid, lactic acid, hydroxyacrylic acid, oxybutyric acid, glyceric acid, malic acid, tartaric acid and citric acid. Examples of the inorganic acids include phosphoric acid, sulfuric acid, nitric acid and hydrochloric acid. Among these acids, preferred are organic acids, more preferred are α-hydroxycarboxylic acids, and even more preferred are lactic acid and malic acid.

Further, the water-based conditioner of the present invention may also contain the water-insoluble modified silicone which are contained as the component (B) in the water-based shampoo of the present invention.

In the water-based conditioner, two or more kinds of the components (B) may be used in combination with each other. The content of the component (B) in the water-based conditioner is preferably from 0.01 to 5% by weight, more preferably from 0.05 to 3% by weight and even more preferably from 0.1 to 2% by weight in view of enhancing the chroma of hair and maintaining a high chroma of hair for a long period of time as well as imparting the hair with a good smoothness after rinsing or drying.

In addition, the water-based conditioner of the present invention may also contain a polyhydric alcohol. Examples of the polyhydric alcohol include glycols having two hydroxyl groups, glycerols having three hydroxyl groups, sugars or reducing sugars, and condensates of the polyhydric alcohols such as glycols and glycerols. Specific examples of the polyhydric alcohol include ethylene glycol, propylene glycol, 1,2-butylene glycol, 1,3-butylene glycol, 3-methyl-1,3-butylene glycol, dipropylene glycol, hexylene glycol, glycerol, trimethylolpropane, pentaerythritol, xylitol, sorbitol and mannitol. Among these polyhydric alcohols, preferred are propylene glycol and glycerol, and more preferred is glycerol.

The polyhydric alcohols may be used alone or in combination of any two or more thereof. The content of the polyhydric alcohol in the water-based conditioner of the present invention is preferably from 5 to 70% by weight, more preferably from 10 to 65% by weight and even more preferably from 15 to 60% by weight in view of a well-controlled moisture retention effect and liquid properties as well as less elution of dyes when treating the colored hair therewith.

Further, the water-based conditioner of the present invention may also contain dimethyl polysiloxane. The dimethyl polysiloxane preferably has a viscosity of from $5 \times 10^4$ to $5 \times 10^7$ mPa·s, more preferably from $10 \times 10^4$ to $2.5 \times 10^7$ mPa·s and even more preferably from $50 \times 10^4$ to $1 \times 10^7$ mPa·s.

The content of the dimethyl polysiloxane in the water-based conditioner of the present invention is preferably from 0.01 to 10% by weight, more preferably from 0.1 to 7% by weight and even more preferably from 0.1 to 5% by weight in view of good smoothness and a silky feel after drying. Further, in view of ease of handling, the dimethyl polysiloxane is preferably diluted with a cyclic silicone or dimethyl polysiloxane having a viscosity of 10 to 10000 mm$^2$/s and then blended in the water-based conditioner.

Moreover, the water-based conditioner of the present invention may also contain, in addition to the above components, various other components and additives according to requirements. Specific examples of the other components and additives include those similarly used in the water-based shampoo such as thickening agents, oils and fats, conditioning agents, ultraviolet absorbers, antioxidants, preservatives, anti-dandruff agents, germicides, pH controllers, sequestering agents and other extracts and dyes derived from animals and plants.

The type of the water-based conditioner of the present invention is not particularly limited as long as the conditioner is of a wash-out type after shampooing, and may be in the form of a liquid, a gel or a cream.

As usual, an appropriate amount of the water-based shampoo of the present invention may be applied to hair wetted with warm water, fully foamed or lathered, and then rinsed with warm water. Thereafter, an appropriate amount of the water-based conditioner of the present invention may be applied to the shampooed hair and intimately spread thereover, and then immediately or after allowing the hair to stand for several minutes, rinsed with warm water.

In accordance with the method of the present invention, dull-color hair damaged due to chemical treatments or daily hair care can be allowed to look clear and vivid as the inherent color of hair, and the chroma can be enhanced thereof.

Also, hair colored with permanent hair dye or semi-permanent hair dye is gradually decolored upon repeated shampooing, etc., so that the increase in a chroma thereof is offset and unexpectable. On the other hand, according to the present invention, clearness of colored hair as well as clearness of color of the hair can be strengthened and maintained for a long period of time.

When any hair is repeatedly shampooed and rinsed according to the present invention, the chroma of the hair can be kept at a high level and can be prevented from being lowered.

The following examples further describe and demonstrate embodiments of the present invention. The examples are given only solely for the purpose of illustration and are not to be construed as limitations of the present invention.

EXAMPLES

Examples 1 to 6 and Comparative Examples 1 to 8

Water-based shampoos and water-based conditioners shown in Tables 4 and 5 were prepared and tested by the following testing methods to evaluate an appearance of the water-based shampoos and observe the condition of modified silicone dissolved therein using an optical microscope. Further, bleached hair and colored hair were tested to examine the change in chroma thereof.

(Observation of Water-based Shampoo Using Optical Microscope)

The condition of the modified silicone dissolved in the water-based shampoo was observed using an optical microscope at -a magnification of 1000 times, and the observation results were evaluated on the basis of the following criteria.

A: No particles of modified silicone were observed

B: Particles of modified silicone were observed (Observation of Appearance of Water-based Shampoo by the Naked Eyes)

The appearance of the water-based shampoo was evaluated on the basis of the following criteria.

A: No particles of modified silicone were observed.

B: Particles of modified silicone were observed as white turbidity or bluish appearance.

C: Separate lower non-water layer was observed irrespective of whether or not the modified silicone is contained therein.

(Polarizing Observation of Water-based Shampoo)

Using a polarizing observation box which was formed by cutting out opposing two walls of a black shielding box and fitting thereto two polarizing films respectively having polarization characteristics perpendicular to each other, the structure of a transparent shampoo solution was observed and evaluated. Specifically, a transparent container filled with the water-based shampoo was introduced into the polarizing observation box. The container was irradiated with light through one of the polarizing films, and the transparent shampoo filled in the container was observed through the other polarizing film by the naked eyes.

A: The shampoo exhibited an isotropy in a static state, but exhibited an anisotropy upon shaking.

B: The shampoo exhibited an anisotropy even in a static state C: The shampoo exhibited an isotropy both in a static state and upon shaking (Change in Chroma of Hair)

(1) Preparation of Bleached Tress

About 20 cm long caucasian light blue hairs which have never been subjected to chemical treatments such as permanent treatment were accurately weighed in an amount of 2.5 g, and roots thereof were fixed together to prepare a tress.

Bleaching agents 1 and 2 shown in Table 1 were weighed in an amount of 2.5 g for each, uniformly mixed with each other, and then uniformly applied to the tress.

TABLE 1

| Components | wt % |
|---|---|
| Bleaching agent 1 | |
| Aqueous ammonia (28 wt %) | 10 |
| Ammonium hydrogencarbonate | 15 |
| Pure water | Balance |
| Bleaching agent 2 | |
| Aqueous hydrogen peroxide solution (35 wt %) | 15 |
| Cetanol | 2.5 |
| Stearyl trimethyl ammonium chloride (63 wt %) | 4 |
| Oxyquinoline sulfate | 0.05 |
| Phosphoric acid | Amount capable of adjusting pH to 3.5 |
| Perfume | 0.5 |
| Pure water | Balance |

The tress was wrapped with a wrapping paper, allowed to stand at room temperature for 30 min, and then rinsed with a flowing tap water maintained at 30° C. Then, the tress was once washed with 0.5 g of a shampoo shown in Table 2, rinsed with water, and then blown and dried with cold air using a dryer.

TABLE 2

| Components | wt % |
|---|---|
| Sodium laurylethersulfate | 17.0 |
| Lauric acid diethanol amide | 2.0 |
| Perfume | 0.5 |
| Citric acid | Amount capable of adjusting pH to 6 |
| Pure water | Balance |

At that time, a lightness (L) and a chromaticity (a: redness; b: yellowness) of the tress was measured at front and rear points of each of root, mid and tip of the tress, i.e., at 6 points in total, using a color difference meter "CR-300" available from MINOLTA CO., LTD., to calculate an average of the measured values. The tress having an L value of 31±1.5, an a value of 18.5±2.0 and a b value of 14.5±1.5 in average was selected and used as a bleached tress to be tested.

(2) Preparation of Colored Tress

Hair color agents 1 and 2 shown in Table 3 were weighed in an amount of 2.5 g for each, uniformly mixed with each other, and then uniformly applied to the tress selected in the above (1). The tress was wrapped with a plastic wrap, and then allowed to stand at 30° C. Thereafter, the tress was rinsed with a flowing tap water maintained at 30° C. Successively, the tress was once washed with 0.5 g of a shampoo shown in Table 2, rinsed with tap water maintained at 30° C., and then blown and dried with cold air using a dryer. At that time, a lightness and a chromaticity of the tress was measured at front and rear points of each of root, mid and tip of the tress, i.e., at 6 points in total, using a color difference meter "CR-300" available from MINOLTA CO., LTD., to calculate an average of the measured values. The tress having an L value of 39±1.0, an a value of 9.5±0.5 and a b value of 19±1.0 in average was selected and used as a colored tress to be tested.

TABLE 3

| Components | wt % |
|---|---|
| Hair color agent 1 | |
| Aqueous ammonia (28 wt %) | 5.0 |
| Monoethanol amine | 2.0 |
| Cetanol | 8.5 |
| 2-methyl-5-hydroxyethylaminophenol | 0.4 |
| 4-amino-2-hydroxytoluene | 0.3 |
| p-aminophenol | 0.3 |
| Phenylene diamine | 0.3 |
| Resorcinol | 0.01 |
| Polyoxyethylene (40) cetyl ether | 3.0 |
| Polyoxyethylene (2) cetyl ether | 3.5 |
| Stearyl trimethyl ammonium chloride | 2.0 |
| Liquid paraffin | 0.5 |
| Sodium sulfite | 0.5 |
| Ascorbic acid | 0.5 |
| Tetrasodium edetate | 0.1 |
| Perfume | 0.4 |
| Ammonium chloride | Amount capable of adjusting pH to 10 |
| Pure water | Balance |
| Hair color agent 2 | |
| Aqueous hydrogen peroxide solution (35 wt %) | 17.0 |
| Phosphoric acid | Amount capable of adjusting pH to 3.5 |
| Pure water | Balance |

(3) Test for Measuring Change in Chroma

After wetting the bleached tress obtained in the above (1) and the colored tress obtained in the above (2) with tap water maintained at 30° C., 0.5 g of the water-based shampoo of the present invention was applied to each tress, and intimately and uniformly spread over the tress with fingers by 30 strokes for 30 seconds for foaming. After the tresses were rinsed with a flowing tap water maintained at 30° C. for 30 seconds, 0.5 g of the water-based conditioner of the present invention was applied to each tress, intimately and uniformly spread over the tress with fingers by 30 strokes for 30 seconds, and then allowed to stand for 5 min. Successively, the tresses were rinsed with a flowing tap water maintained at 30° C. for 30 seconds, and then blown and dried with cold air using a dryer. The above procedure was repeated 10 times. At the time of completing each of the 1st, 3rd, 5th and 10th treatments, the chroma ($c=\sqrt{(a^2+b^2)}$) of each tress was measured at front and rear points of each of root, mid and tip of the tress, i.e., at 6 points in total, using a color difference meter "CR-300" available from MINOLTA CO., LTD., to calculate an average of the measured values. The difference in chroma between before and after each treatment was calculated as change in chroma of the tress. The results as to the bleached tress are shown in Table 4, and the results as to the colored tress are shown in Table 5.

TABLE 4

Evaluation results of bleached tress

| | Examples | | | Comparative Examples | | | | |
|---|---|---|---|---|---|---|---|---|
| | 1 | 2 | 3 | 1 | 2 | 3 | 4 | 5 |
| Water-based shampoo | | | | | | | | |
| Ammonium alkylethersulfate | 10 | 10 | 10 | 10 | 10 | 10 | 10 | 10 |
| Sodium sulfate | 1 | 2 | 2 | 0 | 0 | 0.1 | 10 | 2 |
| Amino-modified silicone*1 | 0.5 | 0.5 | 0.5 | 0 | 0.5 | 0.5 | 0.5 | 0.5 |
| Pure water | AA*2 | AA*2 | AA*2 | AA*2 | AA*2 | AA*2 | AA*2 | AA*2 |
| Observation by optical microscope | A | A | A | — | B | B | — | A |
| Observation by naked eyes | A | A | A | — | B | A | C | A |
| Polarizing observation | A | A | A | — | C | C | B | A |
| Water-based conditioner | | | | | | | | |
| N,N-dimethyloctadecyl-oxy propyl amine | 1.3 | 1.3 | 1.3 | 1.3 | 1.3 | 1.3 | — | *3 |
| Lactic acid | 0.33 | 0.33 | 0.33 | 0.33 | 033 | 0.33 | — | |
| Stearylalcohol | 3 | 3 | 3 | 3 | 3 | 3 | — | |
| Amino-modified silicone*1 | 0 | 0 | 0.5 | 0 | 0 | 0 | — | |
| Pure water | AA*2 | AA*2 | AA*2 | AA*2 | AA*2 | AA*2 | — | |
| Result | | | | | | | | |
| Change in chroma | 0.54 | 0.51 | 0.53 | 0.39 | 0.44 | 0.37 | — | −0.26 |
| 1st treatment | | | | | | | | |
| 3rd treatment | 0.76 | 0.76 | 0.77 | 0.28 | 0.27 | 0.40 | — | −0.22 |
| 5th treatment | 0.72 | 0.72 | 0.95 | 0.21 | 0.11 | 0.16 | — | −0.03 |
| 10th treatment | 0.70 | 0.78 | 1.01 | 0.04 | 0.05 | 0.15 | — | 0.25 |

Note
*1: Amino-modified silicone "XF42-B1989" available from GE Toshiba Silicone
*2: AA = appropriate amount
*3: Treated with only shampoo but no conditioner.

TABLE 5

Evaluation results of colored tress

| | Examples | | | Comparative Examples | | |
|---|---|---|---|---|---|---|
| | 4 | 5 | 6 | 6 | 7 | 8 |
| Water-based shampoo | | | | | | |
| Sodium alkylethersulfate | 15 | 15 | 15 | 15 | 15 | 15 |
| Sodium sulfate | 2 | 5 | 2 | 0 | 0 | 0.1 |
| Bis(C13–15 alkoxy)propylene glycol amodimechicone *4 | 0.5 | 0.5 | 0.5 | 0 | 0.5 | 0.5 |
| Pure water | AA*2 | AA*2 | AA*2 | AA*2 | AA*2 | AA*2 |
| Observation by optical microscope | A | A | A | — | B | B |
| Observation by naked eyes | A | A | A | — | B | A |
| Polarizing observation | A | B | A | — | C | C |
| Water-based conditioner | | | | | | |
| N,N-dimethyloctadecyloxy propyl amine | 1.3 | 1.3 | 1.3 | 1.3 | 1.3 | 1.3 |
| Lactic acid | 0.33 | 0.33 | 0.33 | 0.33 | 0.33 | 0.33 |
| Stearyl alcohol | 3 | 3 | 3 | 3 | 3 | 3 |
| (Bisisobutyl PEG-15/amodimechicone) copolymer*5 | 0 | 0 | 0.5 | 0 | 0 | 0 |
| Pure water | AA*2 | AA*2 | AA*2 | AA*2 | AA*2 | AA*2 |
| Result | | | | | | |
| Change in chroma | | | | | | |
| 1st treatment | 0.24 | 0.18 | 0.11 | −0.31 | 0.02 | 0.05 |
| 3rd treatment | 0.35 | 0.26 | 1.42 | −0.4 | −0.19 | −0.22 |
| 5th treatment | 0.56 | 0.25 | 2.2 | −0.48 | −0.33 | −0.29 |
| 10th treatment | 0.22 | 0.17 | 1.32 | −0.71 | −0.56 | −0.41 |

Note
*4: Bis(C13–15 alkoxy)propylene glycol amodimechicone: "DC8500" available from Toray-Dow Corning Silicone
*5: (Bisisobutyl PEG-15/amodimechicone) copolymer: "FZ-3789" available from Nippon Unicar

INDUSTRIAL APPLICABILITY

According to the method of the present invention, dull-color hair damaged due to chemical treatments or daily hair care can be allowed to look clear and vivid as an inherent color of hair, and the chroma can be enhanced thereof. Also, hair colored with permanent hair dye or semi-permanent hair dye can be strengthened in vividness of hair itself as well as clearness of the color of the hair, and these effects can be maintained for a long period of time.

What is claimed is:

1. A method for enhancing a chroma of hair, comprising the steps of:
   shampooing the hair with a water-based shampoo containing (A) 5 to 20% by weight of an anionic surfactant, (B) 0.1 to 5% by weight of a water-insoluble modified silicone containing at least one of an amino group and a quaternary ammonium group in a molecule thereof, and (C) a water-soluble salt in an amount capable of allowing the component (B) to be present in a solubilized state;
   applying a water-based conditioner containing a higher alcohol having 12 to 28 carbon atoms and a cationic surfactant at a molar ratio of 1:1 to 10:1 to the shampooed hair; and
   rinsing the hair,
   wherein the anion of water-soluble salt (C) comprises an inorganic anion selected from the group consisting of hydrochlorides, sulfates, nitrates, phosphates and chlorates, or an organic anion selected from the group consisting of acetates, citrates, malates, lactates and oxalates.

2. The method for enhancing a chroma of hair according to claim 1, wherein said cationic surfactant is one or more selected from the group consisting of a quaternary ammonium salt, a tertiary amine compound and an acid-added salt thereof.

3. The method for enhancing a chroma of hair according to claim 1, wherein the chroma of hair is kept high even when subjected to repeated shampooing and rinsing treatments.

4. The method for enhancing a chroma of hair according to claim 1, wherein said water-based conditioner further contains the component (B).

5. A method for keeping a color of hair dyed by coloring clear or vivid, comprising the steps of:
   shampooing the hair with a water-based shampoo containing (A) 5 to 20% by weight of an anionic surfactant, (B) 0.1 to 5% by weight of a water-insoluble modified silicone containing at least one of an amino group and a quaternary ammonium group in a molecule thereof, and (C) a water-soluble salt in an amount capable of allowing the component (B) to be present in a solubilized state;
   applying a water-based conditioner containing a higher alcohol having 12 to 28 carbon atoms and a cationic surfactant at a molar ratio of 1:1 to 10:1 to the shampooed hair; and
   rinsing the hair wherein the anion of water-soluble salt (C) comprises an inorganic anion selected from the group consisting of hydrochlorides, sulfates, nitrates, phosphates and chlorates, or an organic anion selected from the group consisting of acetates, citrates, malates, lactates and oxalates.

6. The method for enhancing a chroma of hair according to claim 1, wherein the cation of water-soluble salt (C) comprises lithium, potassium, sodium, ammonium, calcium, magnesium or aluminum.

7. The method for enhancing a chroma of hair according to claim 1, wherein the anion of water-soluble salt (C) comprises a hydrochlorides, sulfate, citrate, malate, or lactate, and the cation of water-soluble salt (C) comprises sodium or ammonium.

8. The method for enhancing a chroma of hair according to claim 1, wherein water-soluble salt (C) comprises sodium sulfate.

9. The method for enhancing a chroma of hair according to claim 1, wherein anionic surfactant (A) is represented by the following formula (1) or (2):

$$R^1O(CH_2CH_2O)_mSO_3M \qquad (1),$$

or $$R^2OSO_3M \qquad (2)$$

wherein $R^1$ is an alkyl group or an alkenyl group having 10 to 18 carbon atoms; $R^2$ is an alkyl group having 10 to 18 carbon atoms; M is an alkali metal, an alkali earth metal, ammonium, alkanol amine or a basic amino acid; m is a number of 1 to 5 in weight-average.

10. The method for enhancing a chroma of hair according to claim 1, wherein anionic surfactant (A) is present in an amount of 10 to 17% by weight.

11. The method for enhancing a chroma of hair according to claim 1, wherein the water-based shampoo additionally comprises a nonionic surfactant, an amphoteric surfactant or a mixture thereof.

12. The method for enhancing a chroma of hair according to claim 1, wherein said molar ratio is 2:1 to 4:1.

13. The method for enhancing a chroma of hair according to claim 1, wherein the higher alcohol comprises stearyl alcohol, behenyl alcohol, or a mixture thereof.

14. The method for enhancing a chroma of hair according to claim 1, wherein the amount of the higher alcohol is 2 to 5% by weight of the water-based conditioner.

15. The method for enhancing a chroma of hair according to claim 4, wherein component (B) is present in an amount of 0.1 to 2% by weight of the water-based conditioner.

16. The method for enhancing a chroma of hair according to claim 1, wherein the water-based conditioner additionally comprises a polyhydric alcohol.

17. The method for enhancing a chroma of hair according to claim 1, wherein the water-based conditioner additionally comprises a dimethyl polysiloxane.

18. The method for enhancing a chroma of hair according to claim 9, wherein anionic surfactant (A) is represented by said formula (1).

* * * * *